United States Patent [19]

Eason et al.

[11] Patent Number: 5,392,209
[45] Date of Patent: Feb. 21, 1995

[54] METHOD AND APPARATUS FOR PROVIDING A DATA INTERFACE BETWEEN A PLURALITY OF TEST INFORMATION SOURCES AND A DATABASE

[75] Inventors: Reginald Eason, Gurnee; Keith Forrest, Deerfield, both of Ill.

[73] Assignee: Abbott Laboratories, Abbott Park, Ill.

[21] Appl. No.: 992,550

[22] Filed: Dec. 18, 1992

[51] Int. Cl.⁶ .......................................... G06F 15/403
[52] U.S. Cl. ................................................ 364/413.01
[58] Field of Search ................ 395/500, 800; 364/413

[56] References Cited

U.S. PATENT DOCUMENTS 4,281,315 7/1981 Bauer et al. ...................... 364/222.2
4,485,439 11/1984 Rothstein ............................ 364/223
4,695,955 9/1987 Faisandier ...................... 364/413.03

Primary Examiner—Donald E. McElheny, Jr.
Attorney, Agent, or Firm—Lawrence S. Pope

[57] ABSTRACT

A data interface which is capable of receiving test information from a variety of biological fluid testing instruments employs first and second processes. The first process determines the type of data which is provided by analyzing the format of the test information using a master rules file. Once the type of the source is identified, the first process passes the data and a set of rules to use to parse the data to the second process. The second process extracts the test data from the information provided by the testing instrument using the set of rules identified by the first process. Furthermore, if the test information is received in pieces the present invention can marry the pieces to provide a complete data set to be stored in the database.

22 Claims, 12 Drawing Sheets

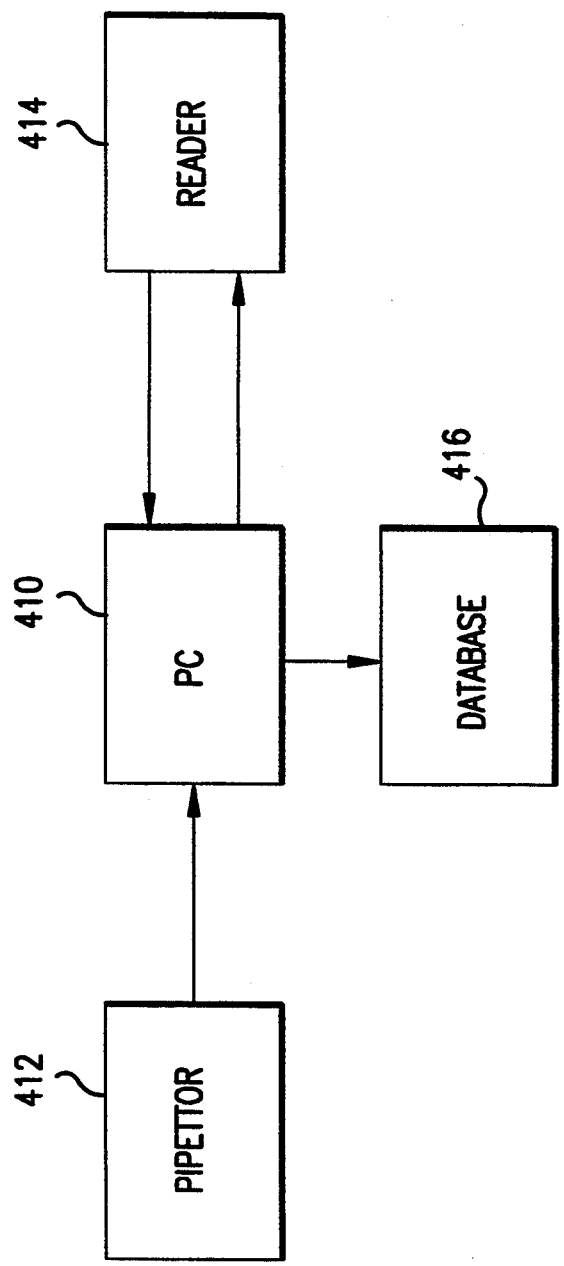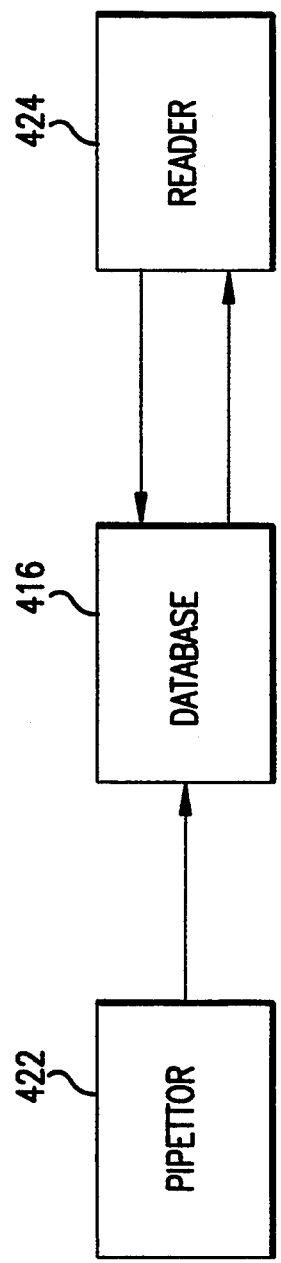

710
THIS IS A HBS EDI TYPE RUN FILE
1-23 "MICROTITER RESULTS DATA"
1-18 "TEST NAME: HBS EDI" : "/usr2/bbs/demon/rules/rules.hbs "
712   # HCV
1-23 "MICROTITER RESULTS DATA"
1-18 "TEST NAME: HCV EDI" : "/usr2/bbs/demon/rules/rules.hcv "
CHV
1-23 "MICROTITER RESULTS DATA"
1-11 "NEG CONTROL"
1-11 "POS CONTROL"
1-18 "TEST NAME: CMV EDI" : "/usr2/bbs/demon/rules/rules.cmv "
HBC
1-23 "MICROTITER RESULTS DATA"
1-18 "TEST NAME: HBC EDI" : "/usr2/bbs/demon/rules/rules.hbc "
HTLV-1
1-23 "MICROTITER RESULTS DATA"
1-21 "TEST NAME: HBC EDI" : "/usr2/bbs/demon/rules/rules.htlv"
CMV
1-23 "MICROTITER RESULTS DATA"
1-21 "NEGATIVE CONTROL MEAN"
1-18 "TEST NAME: CMV EDI" : "/usr2/bbs/demon/rules/rules.bemv"
EDI TYPING
2-3 "DO" :"/usr2/bbs/demon/rules/rules.oly"
ALT
1-6 "MP7000":"/usr2/bbs/demon/rules/rules.alt "

FIG.7

810 — BATCH_NAME "ALT"

812 — TRAY_ID ( 1-7 "TRAY #1" 8-14 )
808 — TECH_ID ( 1-8 "TECH ID:" 9-15 )

HEADING ( 1-6 "HP7000" )

814 — CONTROL ( 14-16 "LCW" 20-22 "LCW" 1-3 )
CONTROL ( 14-16 "MID" 20-22 "MID" 1-3 )
CONTROL ( 13-16 "HIGH" 20-22 "HIGH" 1-3 )
CONTROL ( 13-16 "LSTD" 20-22 "LSTD" 1-3 )
CONTROL ( 13-16 "HSTD" 20-22 "HSTD" 1-3 )
CONTROL ( 12-16 "LVL-1" 20-22 "LVL-1" 1-3 )

816 — SAMPLE_ID : 7-16
818 — TPOS : 1-3
820 — SAMPLE_A88: 20-22
822 — SUBNAME ALT : INTRP : 27-27

824 {
    "L"    LOW
    "N"    NORM
    "E"    ELEV
    "8"    SUPER
    "\?"    RED
    ",*"    NONE
}

FIG.8a

| | | | |
|---|---|---|---|
| A01 | 000000LSTD | | |
| A02 | 000000HSTD | | |
| A03 | 0000000LOW | 004 | L |
| A04 | 0000000MID | 029 | N |
| A05 | 000000HIGH | 068 | E |
| A06 | 00000LVL-1 | 003 | L |
| A07 | 2222200001 | 022 | N |
| A08 | 2222200002 | 037 | L |
| A09 | 2222200003 | 310 | S |
| A10 | 2222200004 | 205 | S |
| A11 | 2222200005 | 007 | N |
| A12 | 2222200006 | 061 | N |
| B01 | 2222200007 | 075 | N |
| B02 | 2222200008 | 011 | N |
| B03 | 2222200009 | ??? | ? |
| B04 | 2980000111 | 047 | N |
| B05 | 2222200011 | 052 | ? |
| B06 | 2222200012 | 050 | N |
| B07 | 2222200013 | 024 | N |
| B08 | 2222200014 | 008 | L |
| B09 | 2222200015 | 010 | N |
| B10 | 2222200016 | 062 | E |
| B11 | 2222200017 | 099 | E |
| B12 | 2980000119 | 038 | N |
| C01 | 2222200019 | 012 | N |
| C02 | 2222200020 | 089 | E |
| C03 | 2222200021 | 102 | S |
| C04 | 2222200022 | 021 | N |

FIG.8b

```
BATCH_NAME    "CMV"
PROCEDURE   { 1-10 "TEST NAME:" 12-20 }
TRAY_ID     { 1-14 "ASSAY TRAY ID:" 16-12 }

HEADING  { 1-10 "MICROTITER" }
HEADING  { 1-11 "TRAY STATUS" }
HEADING  { 1-9  "TEST DATE" }
HEADING  { 1-4  "QC-6" }
HEADING  { 1-5  "LVL-1" }
HEADING  { 1-5  "LVL-2" }
HEADING  { 1-5  "LVL-3" }
HEADING  { 1-12 "END OF BATCH" }

MASTER_LOT  { 1-11 "MASTER LOT:" 13-19 }

CONTROL  { 6-13  "NEG_CNTL" 16-21 "NEG" 1-3 }
CONTROL  { 6-13  "POS_CNTL" 16-21 "POS" 1-3 }
CONTROL  { 6-13  "POS_CNTL" 16-21 "POS-2" 1-3 }

CNTRL_AVERAGE  { 1-22 "NEGATIVE CONTROL MEAN:" 24-29 NEG_TYPE }
CNTRL_AVERAGE  { 1-22 "POSITIVE CONTROL MEAN:" 24-29 POS_TYPE }
CNTRL_AVERAGE  { 1-24 "POSITIVE-2 CONTROL MEAN:" 26-31 POS2_TYPE }
CNTRL_RANGE    { 1-15 "NEGATIVE RANGE:" 17-32 POS_TYPE }
CNTRL_RANGE    { 1-15 "POSITIVE RANGE:" 17-32 NEG_TYPE }
CNTRL_DIFF     { 1-13 "CONTROL DIFF:" 15-20 NEG_TYPE }

CUTOFF  { 1-13 CUTTOFF VALUE: 15-20 }

SAMPLE_ID  : 2f
TPOS       : 1f
SAMPLE_ABS : 3f

SUBNAME CMV : INTRP : 4f
{
        "\*\*\*"       NEG
        "REACTIVE"     POS
        "*"  ""        NONE
}
```

FIG.8c

METHOD AND APPARATUS FOR PROVIDING A DATA INTERFACE BETWEEN A PLURALITY OF TEST INFORMATION SOURCES AND A DATABASE

FIELD OF THE INVENTION

The present invention relates generally to a data interface and, more particularly, to an data interface which enables a database to collect and maintain test information related to biological fluids from different types of test information sources.

BACKGROUND OF THE INVENTION

There are many reasons for testing biological fluids. For example, the donation of blood typically requires that the blood be screened for various diseases and/or foreign bodies. Blood screening of donors at blood banks is a large and ever growing market requiring accurate and reliable testing. Other biological fluids, such as urine and saliva, are routinely tested and/or screened to detect diseases, chemicals or other substances.

Over the years, as both the amount of blood being donated and the number of required tests have increased, a degree of automation has occurred. Systems such as the Commander System TM by Abbott Laboratories, have partially automated many of the steps involved in blood testing.

The Commander System TM can be divided into four main parts: a Flexible Pipetting Center (FPC) which transfers samples to test wells in sample trays, a Parallel Processing Center (PPC) which adds reagents and reads optical absorption test results, a Dynamic Incubator (DI) which incubates the samples, and a Data Management System (DMS) which stores the test results for access by other programs. Under this system, a donor's blood sample is initially bar coded. This information is stored in a local database with the same information residing in the DMS database. The bar coded samples are then transferred to the FPC for pipetting into test wells. The bar coded blood samples have their exact well position in the holding tray entered into the database. This position information is supplied by the FPC in pipetting the samples and is used by the PPC and DMS.

Each holding tray is also bar coded. This bar code is read as soon as the tray is placed into the FPC. The bar code information on the tray, combined with the bar code information on each blood sample, provides for accurate data gathering and tracking of the blood samples through the testing process.

Next, the tray containing the samples moves either to the DI or to the PPC, depending upon the tests being run. As an example, assume the tray moves next to the PPC, the bar code of the tray is again read, to insure tracking of each individual blood sample contained in the test wells. A connection, such as a serial data connection, links the FPC to the PPC to track the blood sample through the entire testing procedure. The PPC reads the test results. The test results, which are linked to a particular blood sample by way of the bar code, are then ported over to the DMS via, for example, a serial data connection.

The DMS takes the information provided to it from the PPC to provide a report of the test results for each blood sample.

In the example of the Commander System TM, the system components are linked by a communication interface which allows for a continuous "chain-of-custody" to be established for the tested samples. This is illustrated in FIG. 1a, in which, pipettor 110 passes its information along to reader 112 which, in turn, passes a complete package of test information to database 114.

Because many vendors produce biological fluid testing instruments, however, multi-vendor testing environments are commonplace. FIG. 1b illustrates a possible configuration, where a pipettor 120 and a PPC 122 are not compatible and, hence, not linked by a communication interface. In this case, pipettor 120 passes its information to database 114 where it is temporarily stored. Subsequently, PPC 122 requests the pipettor information from database 114 via a special driver; links the test results, which were obtained by reading the sample tray, with the pipettor information; and passes the complete package back to database 114.

In systems of this type, in order to accommodate the numerous system configurations that may arise, database 114 desirably interfaces with a variety of potential sources of test information.

FIG. 2 shows an example of a data interface for the database 114 of FIG. 1a. In FIG. 2, reader 210 sends test information to driver 212 which handles the communication interface and completed receipt of the test information. The test information is then processed by demon 214 which parses the data file and enters it into database 114. The word "demon" as used herein means a process running on one of the computer systems which are coupled to the system. Although the term as it is used in the art typically designates a background process which does not terminate, the present usage of the word is not so limited.

In the system shown in FIG. 2, the reader 210 can be one of several different instruments. Examples of such include a PPC TM, a Quantum II TM, a Quantumatic TM or a VP TM all made by Abbott Laboratories.

FIG. 3 shows an example interface used for the system configuration of FIG. 1b in which pipettor 310 supplies information to database 114. The interface of FIG. 3, similar to that of FIG. 2, uses a separate driver 312 and demon 314 combination for each pipettor supplying information. However, in FIG. 2, the information is only temporarily stored in database 114 until it is requested by PPC 122 (FIG. 1b). The pipettor information is then transferred via a special driver, PPC_com 318, to PPC 122 which reads and delivers a complete test information package to database 114 via the interface configuration of FIG. 3.

The requirement that different drivers and demons be created and used for each new system configuration is complicated, time-consuming and impedes the efficient development and integration of multi-vendor testing environments.

SUMMARY OF THE INVENTION

In a system for collecting biological fluid test information from any one of several test information sources and maintaining the biological fluid test information in a database, the present invention is embodied in a system which provides an interface between each of several information sources and the database. The data interface includes a driver which automatically adapts itself to communicate with each of the several sources, to receive test information.

According to one aspect of the invention, the system includes a post-demon which, based on the identity of the information source and the corresponding information format, parses test information received from any one of a plurality of information sources. The post-demon also enters the parsed information into the database.

According to another aspect of the invention, the system includes a preprocessing demon (pre-demon) which is used to examine, based on a set of predetermined rules, the received test information to identify its source. Additionally, a postprocessing demon (post-demon) is provided which parses the test information, based on the identification made by the pre-demon using a second set of predetermined rules. The post-demon also enters the parsed information into the database.

According to another aspect of the invention, the system includes a demon which can link or marry partial information records from two sources to generate a complete record.

BRIEF DESCRIPTION OF THE DRAWINGS

The present invention is described by way of nonlimiting example with reference to the following figures in which:

FIG. 2 (prior art) is a functional block diagram of a data interface suitable for use with the prior art configuration of FIG. 1a;

FIG. 4a is a high-level functional block diagram of a biological fluid testing system according to the present invention which employs a processing system to correlate test information before sending it to a database;

FIG. 4b is a high-level functional block diagram of a biological fluid testing system according to the present invention in which the pipettor and reader send their information to the database individually;

FIG. 7 is a program listing which shows an example of a master rules file suitable for use with the data interfaces of FIGS. 5a and 5b;

FIG. 8a is a program listing which shows an example of a rules file suitable for use with the data interfaces shown in FIGS. 5a and 5b;

FIG. 8b is a program listing which shows an example of a run file, used by the data interfaces shown in FIGS. 5a and 5b and described by the rules file shown in FIG. 8a;

FIG. 8c is a program listing which show an example of an alternative rules file, used by the data interfaces shown in FIGS. 5a and 5b;

DETAILED DESCRIPTION OF THE INVENTION

I. Overview

Figure 1A:
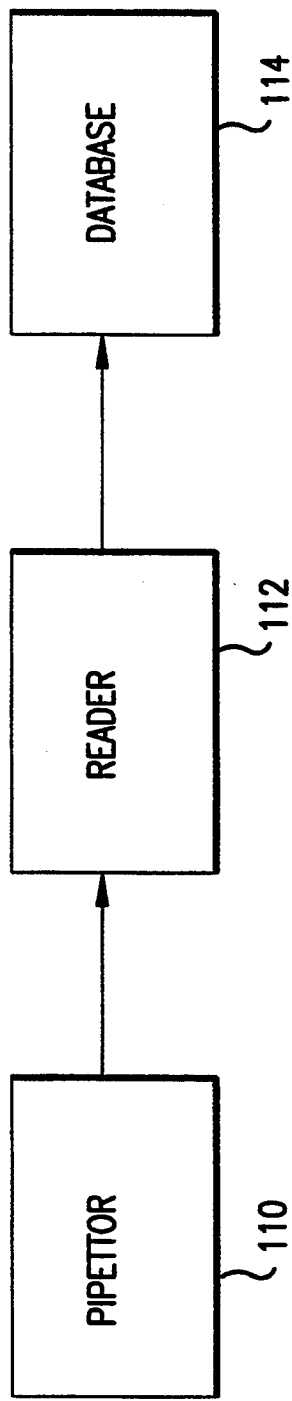
FIG. 1a (prior art) is a high-level functional block diagram of a prior art biological fluid testing system configuration employing a compatible pipettor and reader.
Figure 1B:
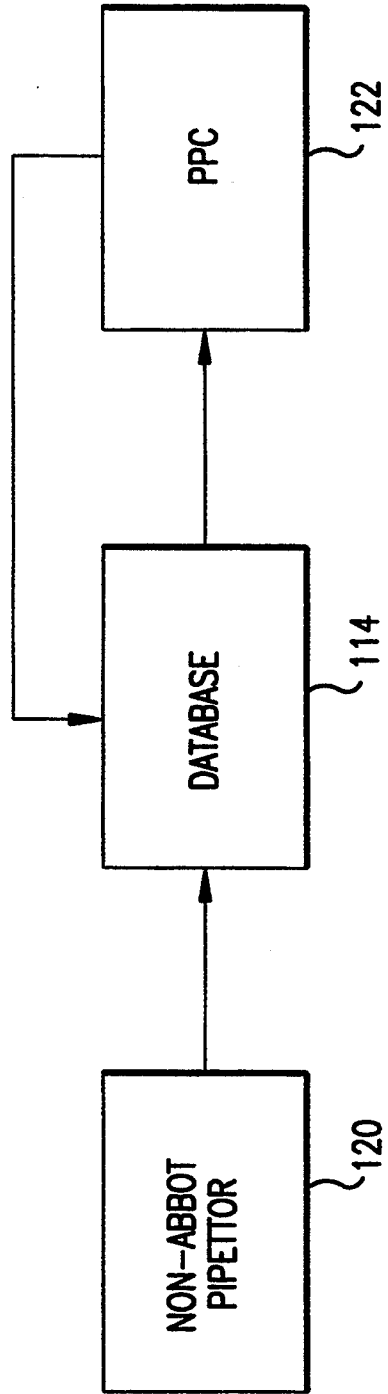
FIG. 1b (prior art) is a high-level functional block diagram of a prior art biological fluid testing system configuration employing a non-compatible pipettor and reader.
Figure 2:
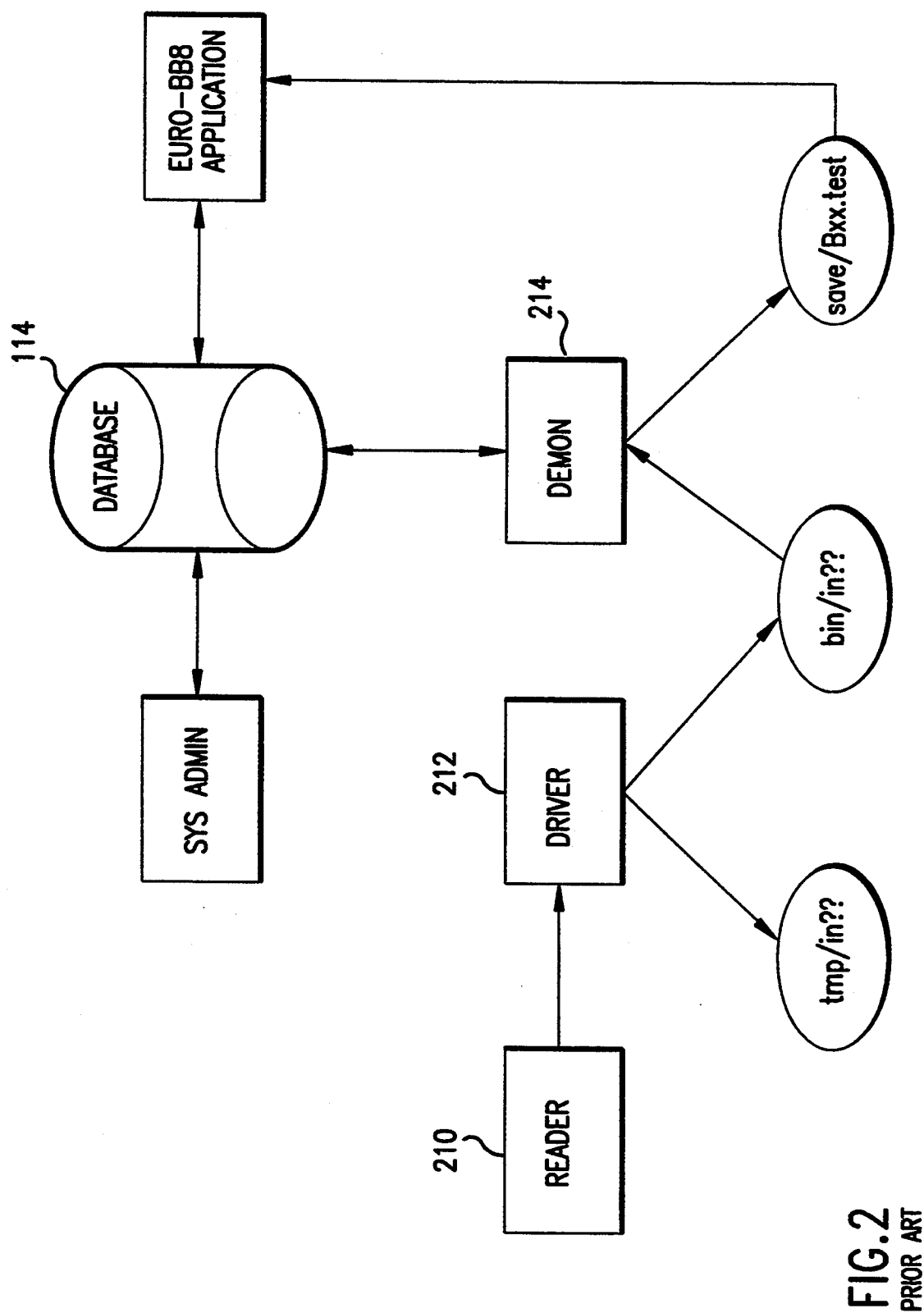
Figure 3:
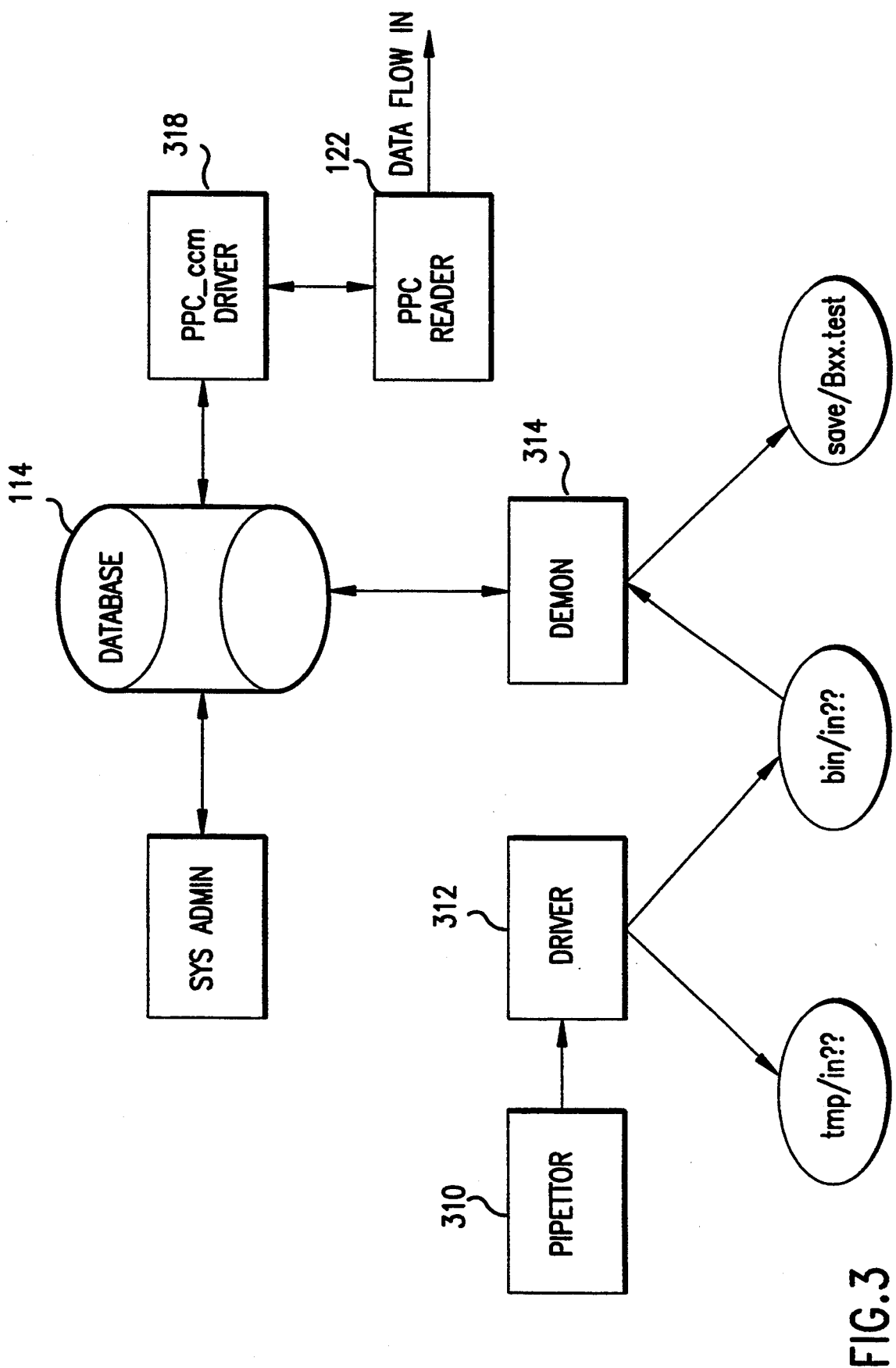
FIG. 3 (prior art) is a functional block diagram of a data interface suitable for use with the prior art configuration of FIG 1b, in combination with the interface of FIG. 2.

The present invention provides a data interface for a database which receives and maintains test information which may be generated by a variety of different sources having a variety of different formats. In the exemplary embodiment of this invention, the test information is related to test results of biological fluids.

As mentioned, the test information may be generated by a variety of instruments, for example, test information related to the identification of fluid samples in a tray can be generated by pipettors. Test results associated with the fluid samples can be generated by equipment which adds reagents to the samples and then analyzes the light transmitted through the samples once the reaction is complete. The portion of this equipment which generates the data values is generically known as a reader. Both readers and pipettors are available from many different vendors. In addition, other types of information about the biological fluids may be developed using other types of instruments which measure sample properties other than optical absorption. Consequently, many different types of test information can be collected and maintained in a database and the data may be provided in many different formats.

FIGS. 4a and 4b, by way of example, illustrate two contemplated system configurations for collecting test information. In FIG. 4a, data processing system 410, such as a personal computer (PC), controls and coordinates the activities of a pipettor 412 and a reader 414. First, pipettor 412 loads the wells of a tray to be tested with fluid samples. The identification information associated with the tray and the samples is passed by the pipettor 412 to the PC 410. Next, reader 414 performs the selected test(s) on the tray previously prepared by pipettor 412. The results of the test(s) are sent to PC 410 which couples the pipettor information and the reader information. PC 410, then, passes a complete test information file to database 416. A database system suitable for use as the database 416 is the Euro Blood Bank System (EURO-BBS TM) which is manufactured by Abbott Laboratories.

In contrast, FIG. 4b illustrates a system configuration not governed by a separate local data processing system. In FIG. 4b, pipettor 422 passes its information to database 416 first, then, after the samples are tested, reader 424 passes its results to database 416. In this case, the test information is received in pieces. In this example, the processing functions performed by the PC 410 of FIG. 4a may be consolidated in processing hardware coupled to the pipettor 422, database 416 or reader 424. Alternatively, these functions may be distributed among this processing hardware.

As seen from FIGS. 4a and 4b, depending on the system configuration, the test information can be sent to database 416 from various sources (e.g., PC 410, pipettor 422 or reader 424). Thus, the present invention enables the database 416 to receive and maintain test information from a variety of sources.

Figure 5A:
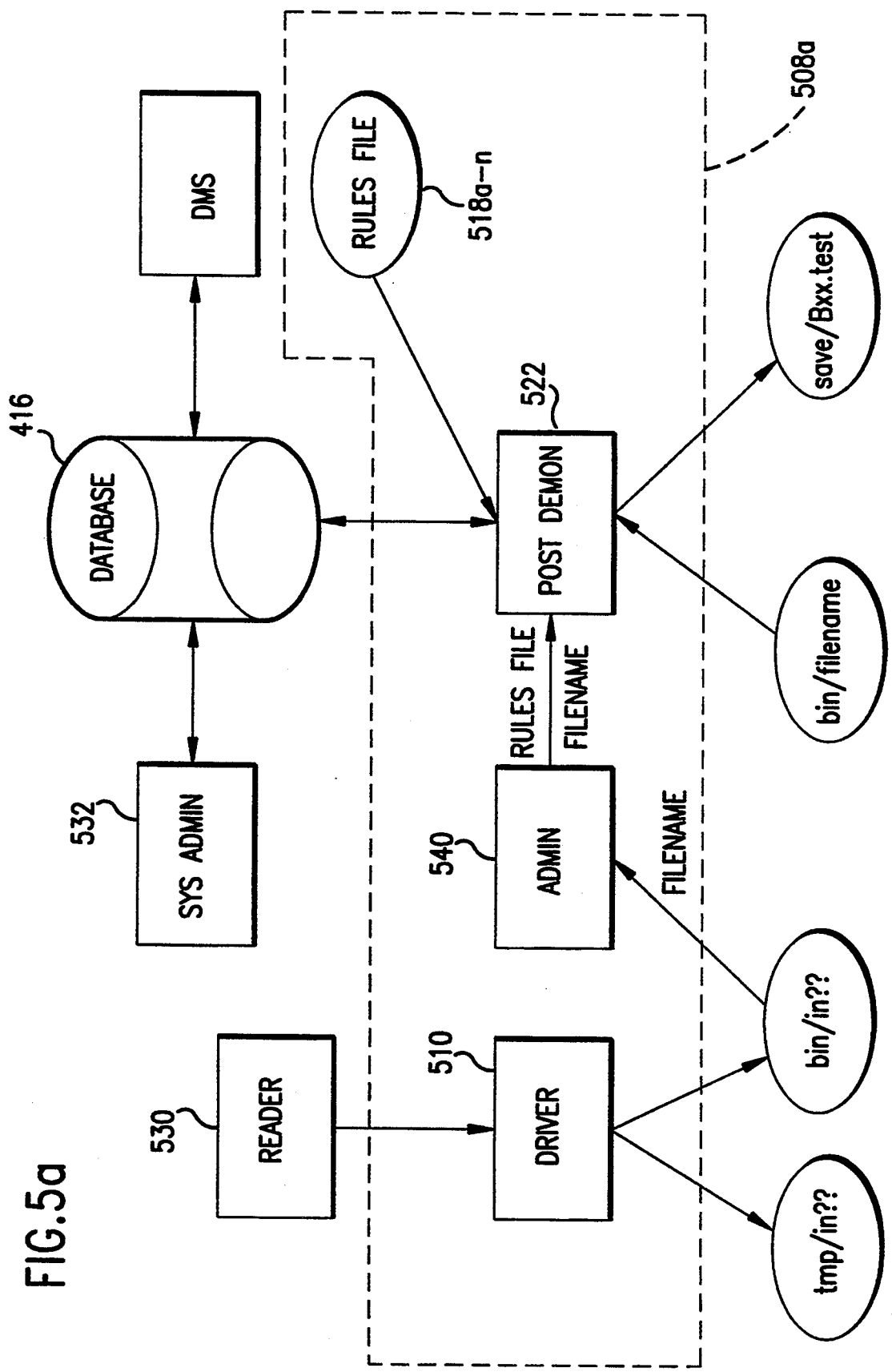
FIG. 5a is a functional block diagram which shows a first embodiment of a data interface, employing a post-demon, suitable for use with the present invention.

FIG. 5a is a first embodiment of a data interface 508a suitable for use with the present invention. Data interface 508a comprises a device driver 510, a post-demon process 522 along with particular rules files 518a-n which are associated with a particular device by a system administrator (ADMIN) 540. In the discussion that follows, the entire data interface 508a (excluding Administrator 540) is assumed to be running on a single computer system, for example, the PC 410 shown in FIG. 4a. It is contemplated, however, that parts of interface 508a may be implemented on respectively different computer systems with the functionality being divided among the pipettor and database processors as well as other processors that may be coupled to the system.

The exemplary environment in which data interface 508a operates includes a source of test information (Which, in this case, is reader 530), a system administrator 532 (an application interface which uses database 416), a database 416 and a data management system (DMS) 533 which allows applications programs (not shown) to access the database.

In FIG. 5a, post-demon 522 parses a received data file and places the information into database 416. Prior to processing the received data file, however, post-demon 522 needs to know the information source type (i.e., the identity of reader 530) and the file format of the received data file so it can properly parse the received data file and enter it into database. In this embodiment of the invention, the source type and file format information are configured by an administrator 540 before the data file is generated. In the exemplary embodiment of the invention, the administrator 540 assigns a particular rules file, corresponding to a respective particular data source type, to a corresponding input port to the post-demon 522. One rules file may be associated with multiple input ports. All data from sources having an identified source type is applied to the post-demon 522 via the input port that has been defined for that source type. This information is parsed using the file format information which is contained in the assigned .one of the rules files 518a-n. Alternatively, the data source may be coupled to the post-demon 522 via a network (not shown). In this configuration, the rules file which is used to parse the data is determined from a directory accessible to the post-demon 522.

Exemplary data source types, in this case, readers 530 include the Olympus ™ PK7100, manufactured by Olympus; the Groupamatic ™ manufactured by Kontron, the Autogrouper ™ manufactured by Technicon or the EPOS ™ manufactured by Eppendorf. To date, driver 312 and demon 314 have been specifically designed to interface with the particular instruments/tests being used/run. Thus, a different driver and demon need to be generated for each instrument/test providing test information to the database 114. The phrase "instrument/test" is used because it is possible for a single instrument to perform two or more different tests having different test information formats each of which needs a separate, dedicated demon to parse the test results.

Figure 5B:
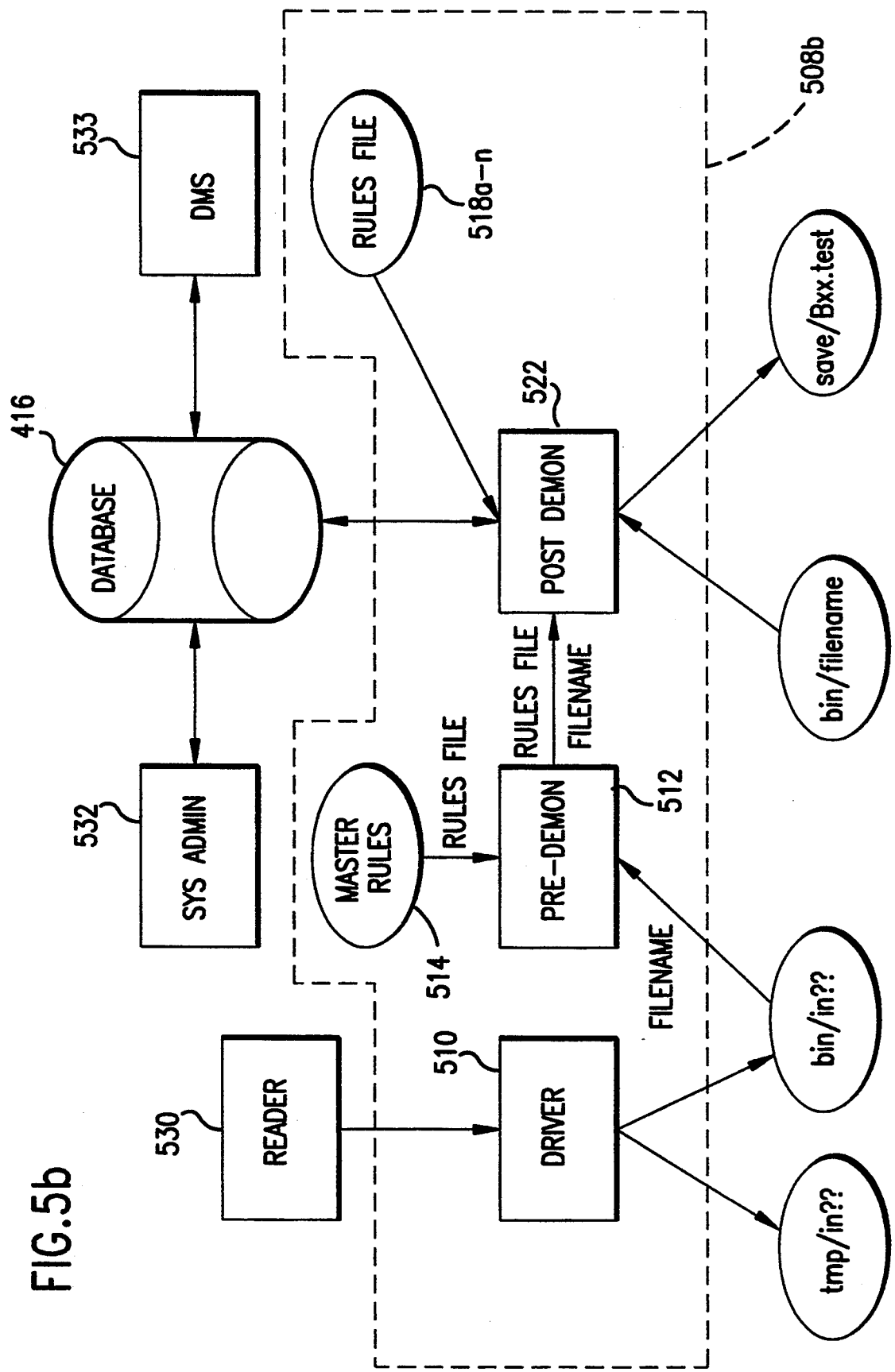
FIG. 5b is a functional block diagram which shows a second embodiment of a data interface, employing a pre-demon and a post-demon, suitable for use with the present invention.

FIG. 5b is a second embodiment of a data interface 508b suitable for use with the present invention. Similar to the interface 508a, Data interface 508b comprises a device driver 510 and a post-demon process 522 along with particular rules files 518a-n. Data interface 508b also includes, however, a pre-demon process 512 along with a master rules file 514. Pre-demon 512 plays the role of administrator 540 in data interface 508a. As above, in the discussion that follows, the entire data interface 508b is assumed to be running on a single computer system, for example, the PC 410 shown in FIG. 4a. It is contemplated, however, that parts of the interface 508b may be implemented on respectively different computer systems with the functionality being divided among the pipettor and database processors as well as other processors that may be coupled to the system.

In FIG. 5b, pre-demon 512, using the master rules file 514, examines the received data file and identifies the source. Next, pre-demon 512 passes the identity of the source (i.e., instrument/test) of the data file along with a format-defining file (or filename) which will enable post-demon 522 to parses the data file and place the information into database 416. Thus, in data interface 508a administrator 540 supplies the source type and file format information, whereas, in data interface 508b pre-demon 512 supplies the source type and file format information.

Post-demon 522, in FIGS. 5a and 5b, can also couple or "marry" test information that has been received in pieces. In other words, if, for example, a pipettor sends its information to the database first, then, a reader sends the results related to the pipettor information subsequently, post-demon 522 can correlate the information and complete the test information package which is entered into the database. A contemplated configuration for which this may occur is illustrated in FIG. 4b.

It should be noted that the marrying of separate pieces of test information need not be limited to post-demon 522. It is contemplated that the data marriage feature could run on a separate demon process or be distributed among two or more demon processes.

In sum, the two described embodiments of the present invention provide a data interface which can: receive test information from a variety of sources; parse the identified test information given the identity of the source and the format of the test information (whether supplied by a user or pre-demon); and properly enter the information into the database 416. Furthermore, if the test information is received in pieces the present invention can marry the pieces to produce a complete test information record.

The practical consequence of a generic data interface is that there is no longer a need for many specialized data interfaces. This consequence is significant in multi-vendor environments which require a high degree of integration and automation to enhance overall efficiency.

II. Detailed Description of the Exemplary Embodiment

A. Data Interface 508a/b

Figure 6:
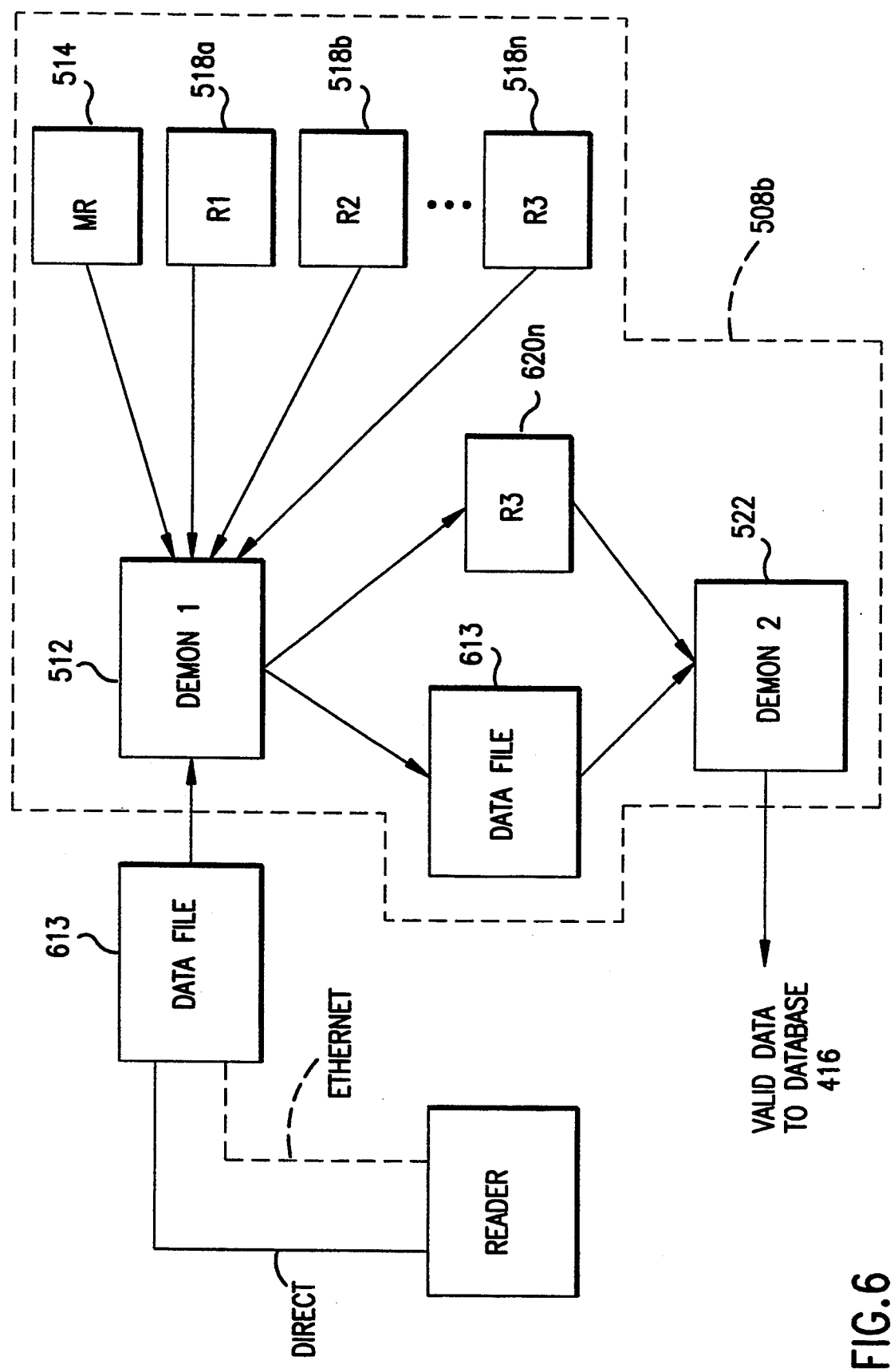
FIG. 6 is a more detailed functional block diagram which illustrates the interaction of the pre-demon and post-demon in the data interface of FIG. 5b.

FIG. 6 is a functional block diagram showing additional detail of data interface 508b of FIG. 5b. Because data interface 508a is virtually a subset of data interface 508b, data interface 508b is described, thus, covering data interface 508a. In FIG. 6, a reader 610 sends test information, represented as data file 613 (also known as a run file), either directly or otherwise (e.g., via an Ethernet network interconnection), to the database. The information is received and initially processed by data interface 508b.

Data interface 508b includes a pre-demon 512 which, based on a set of predetermined rules 518a–n, examines data file 613 and determines the source of the test information. The source designation could be the type of system, possibly, or the type of test (if formats of tests on the same system are different) which produced the test information. In the exemplary embodiment of the present invention, the predetermined rules are contained in rules files 518a–n. In addition, a master rules file 514 is used by the pre-demon 512 to associate each type of data source with a particular rules that is to be used to parse data received from sources of that type.

Data interface 508b also includes a post-demon 522 which, based on the identification made by pre-demon 512, parses the received test information and enters the valid data into database 416. Additionally, post-demon 522 can couple or "marry" test information that has been received in pieces.

Each element of data interface 508b, as well as the manner in which it interfaces with the exemplary embodiment of the invention is described below.

1. Device driver 510

Referring back to FIGS. 5a and 5b, in the exemplary embodiment of the present invention, driver 510 handles the communication interface between source 530 and data interface 508b. Driver 510 can receive data by KERMIT, ACK/NAK, and XON/XOFF protocols based on a configuration parameter which may be specified by the system administrator. The data that may be received may be a single tray batch, a multiple tray batch in which a single set of control samples is provided for several trays, and a multiple single tray batch, in which each tray forms a separate and distinct batch. In this last instance, the driver generates multiple run files, one for each batch.

Interface 508b, via driver 510, can also verify checksums received with the data. The checksum evaluation may also be switched on or off, based on a specified parameter, to prevent checksum evaluation when the data source does not provide a checksum. In addition, the checksum evaluation may use one of a finite set of algorithms configured on the system.

If KERMIT is used, the driver enters a KERMIT server mode awaiting a run file. Once a completed run file is received, no further processing takes place on the file before it is passed to the pre-demon 512. It should be noted that the checksum options are desirably disabled when the KERMIT method of transfer is selected.

The ACK/NAK protocol is most useful when used in conjunction with checksums. If this protocol is used without checksums enabled, the system always sends an acknowledgement (ACK) to the reader and writes the data record to the run file.

If the checksums are enabled, however, the checksum is evaluated after a line of data has been received. If the checksum generated from the received data matches the checksum that was transmitted with the data, the system sends an ACK to the reader and writes the data to the run file. If the checksum check fails, the system sends a negative acknowledgement (NAK) to the reader causing it to retransmit the data. The driver 510 does not write to the run file until data having a valid checksum is received.

If, during the capture of any run file, any record (i.e. line of the file) cannot be obtained with a valid checksum, the entire file is discarded.

XON/XOFF is the most basic of the protocols. In this protocol, driver 510 is merely a conduit to the operating system kernel of the processor on which the system shown in FIG. 5b is implemented. Using this protocol, the system receives the data into data buffers in its main memory. When the system data buffers are nearly full, the operating system sends an XOFF command to stop the transmission of new data. When the buffer has been emptied sufficiently to accept new data, the operating system sends an XON to restart the transmission.

If the checksums are not enabled, every line that is received is added into the run file. If checksums are enabled they are evaluated after each line of data is received.

Although, in the exemplary embodiment, driver 510 is described as handling the KERMIT, ACK/NAK and XON/XOFF protocols, it is understood by one skilled in the art that other forms of protocols and communication links may be used to transfer data files from instruments or other processing systems to the database 416 using the data interface 508.

2. Pre-Demon 512

Pre-demon 512 uses a master rules file 514 to examine the test information received by driver 510 (or directly in the TEMP directory as in the case with run files that are transmitted across the network) in order to identify the type of instrument/test which provided the data and, so, the rules file to be used to transfer the data to the database 416. When data is transmitted across the network, however, the run files are not made available for use by the pre-demon 512 until the file is complete.

Before it processes any run files, pre-demon 512 reads and parses the master rules file 514 to verify that each of its entries are syntactically correct. This processing step enforces a format for the master rules file 514 which is described below in the Master Rules File section with reference to FIG. 7. As described below, each set of rules in the file corresponds to respectively different run file formats.

In the exemplary embodiment of the present invention, every five seconds, pre-demon 512 looks for new run files which may have been generated by driver 510. When a new run file is available, each line of the run file is compared to every rule in master rules file 514. If a line satisfies a rule, then a counter for that rule is incremented. A set of rules is considered the "most satisfied" set if the total value of its counters is greater than the value of the counters of any other set of rules and if each rule in the set of rules has been satisfied.

If no rule sets in the master rules file are satisfied at the end of the run file or if two rule sets are equally satisfied, the data is rejected, and the run file is moved to the save directory.

The one set of rules from the master rules file that most satisfies the run file determines which rules file 518a–n is selected for further processing of the run file. Once this determination has been made, the pre-demon 512 passes the selected rules file 518a–n and the run file (or pointers to the files) to post-demon 522. Pre-demon 512 continues processing new run files while post-demon 522 finishes processing the passed run file.

In the exemplary embodiment of the invention, if the driver process 510, pre-demon process 512 and post-demon process 522 are all running on the same computer system, the rules file and run file may be stored in fixed locations in random access memory (RAM), or on a disk drive. In this instance the passing of this information from one process to another may be accomplished by simply passing the address or file name. Alternatively, if the processes are implemented on different computers, the actual file data may be transferred between the computers.

a. Master rules file 514

A separate master rules file 514 is generated for each location (i.e., bloodbank or other fluid testing facility) depending on the system configuration and the instruments available at that facility which can generate the test information.

An example of a master rules file is shown in FIG. 7. In this Figure, the first test is for information received from an HBS assay. Pre-demon 512, using master rules file 514 as a guide, checks the received data file to determine if columns 1–23 of a line in the file contain the character string "Microtiter Results Data" (step 710), and if columns 1–18 in another line in the file contain the character string "Test Name: HBS EDI" (step 712). If these fields match and no other rule set in the master rules file has a better match, pre-demon 512 has identified the run file as satisfying the master rules for an HBS output. Based on this identification, the pre-demon 512 indicates to post-demon 522 which of the rules files 518a–n to use, in this case, the appropriate rules file would be "/usr2/bbs/demon/rules/rules.hbs" as specified in step 712 of the first set of master rules.

As described above, the pre-demon 512 compares the run file to each set of master rules before it declares a match. This is done because equipment purchased from the same manufacturer may have subtly different data formats as may different tests performed using the same instrument. These differences are reflected by slight differences in the rules in the master rules file which correspond to the different test formats. By checking the run file against all of the rules, the system ensures that the proper set of rules will be used for each instrument or test.

If the second or other set of rules presents a better match than the first set, the pre-demon 512 indicates that the rules file associated with that other set of master rules provided the data that is stored in the run file. At this point, pre-demon 512 indicates to post-demon 522 the appropriate rules file, as listed in the master rules file, to be used to parse the run file.

3. Post-demon 522

Referring back to FIG. 5b, post-demon 522, using the selected rules file 518a–n, parses the data file to extract the relevant test information and enter it into database 416. Additionally, post-demon 522 can perform a data marriage.

First, post-demon 522 checks the selected rules file 518a–n for correctness. The format of rules files 518a–n is described below in the Rules File section with reference to FIGS. 8a–c.

Next, post-demon 522 parses the run file and checks the test information which is extracted. If the information is POSID (the test results are associated with sample IDs) then the information is entered into database 416. If the information is NON-POSID (test results without sample IDs), post-demon 522 may look for the related pipettor information in an attempt to combine or "marry" the separate sets of information. Marrying of information is described below in the Data Marriage section with reference to FIG. 9.

b. Rules Files 518a–n

A separate rules file 518a–n is generated for each type of instrument/test which may provide test information to the database 416 at a particular location. As mentioned, for the present invention, it is contemplated that a variety of sources (e.g., host system, reader, pipettor, or any other instrument/test desiring to place information in the database) can be supported.

Each of these rules files corresponds to the list of rules files in master rules file 514 (see FIG. 7).

The following table, Table 1, shows the basic form of a rules file:

TABLE 1

| Position | Item | Req'd | Zero Or One | Zero Or More | More Than 1 |
|---|---|---|---|---|---|
| 1 | Start | X | | | |
| 2 | BatchName | X | | | |
| 3 | Procedure | | X | | |
| 4 | Tray ID | | X | | |
| 5 | Tech ID | | X | | |
| 6 | Header | | | X | |
| 7 | Master Lot | X | | | |
| 8 | Control | | | X | |
| 9 | Control Avg | | | X | |
| 10 | Control Range | | | X | |
| 11 | Control Diff | | | X | |
| 12 | Cutoff | | X | | |
| 13 | Cutoff Form | | X | | |
| 14 | Sample ID | | X | | |
| 15 | Tray Position | | X | | |
| 16 | Sample Absorbance | | X | | |
| 17 | Sub Batch Info | | | | X |
| 18 | Errors | | | X | |
| 19 | End | X | | | |

It should be noted that there are four groups that form each phase of the parsing of a given line. The reading of every line progresses through each phase starting at phase 1 going through to phase 4. If a line fulfills at least one item in a phase, then the line does not continue to the next phase. Phase 1 contains the Errors item. Phase 2 contains the Header section. Phase 3 contains the Procedure, Tray ID, Tech ID, Header, Master Lot, Control, Control Average, Control Range, and Control Difference items. Phase 4 contains Sample ID, Tray Position, Sample Absorbance, and Sub Batch Info items. These phases are described below in the Run File Processing section with reference to FIG. 8b.

FIG. 8a is an example of one of the rules file listed in the master rules file of FIG. 7 (ALT rules file). And, FIG. 8b is an example run file corresponding to the ALT rules file of FIG. 8a. The rules file of FIG. 8a describes the data format of the run file of FIG. 8b produced by an ALT type information source. This type of information source provides data from an ALT-type liver function test.

With reference to FIGS. 8a and 8b as a preliminary step to processing the run file shown in FIG. 8b, the post demon 522 generates a blank record which will be stored in the database 416 and sets the BATCH-_NAME field of the data record to "ALT". This identifies the data record as containing information concerning the ALT liver function test.

To begin parsing the run file, Post-demon 522, using the rules file as a guide, reads the first line of the run file shown in FIG. 8b. The text on this line, "MP7000" does not match any of the rules in the rules file shown in FIG. 8a and so, is ignored. Next, the second line in the run file is read. This line is parsed by line 808 of the rules file shown in FIG. 8a. To parse this line, the post-demon, at step 808, determines that this is a tech ID line because columns 1–8 contain the character string "Tech ID". Columns 9–15 are identified by the rule at step 808 as containing the actual Tech ID. The post demon retrieves the character string "CHRIS" from these columns and stores the string into the TECH_ID field of the data record for this test.

Next, at step 812, post-demon 522 reads the third line of the run file and determines that this is a tray ID line because columns 1-7 contain the character string "Tray #:." Columns 8-14 contain the actual tray number which is entered into the field TRAY_ID of the database record. Skipping to line 6 of the run file, at step 814, post-demon 522 determines that this is data that defines the low control samples that are used in the tray because columns 14-16 contain the string "LOW". The run file entry for this type of line indicates that columns 20-22 contain the optical absorbance value for the low control sample and that columns 1-3 contain the control position string. The two quoted strings in the rules file step 814 contain the regular expression for the control string and the control type to update in the control table, respectively. The control absorbance information is added to the control table and indexed in the table by the control position string "LOW."

At steps 816, 818, 820, 822, and 824 of the rules file, the post demon 522 is instructed to interpret any line in the run file, which has a ten-character value in columns 7-16, a three-character value in columns 1-3, a three character value in columns 20-22 and a one character value in column 27 as containing data for a test. In the example shown in FIGS. 8a and 8b, the value in columns 7-16 of the run file line is the sample ID, the value in columns 1-3 is the tray position, the value in columns 20-22 is the sample absorbance and the value in column 27 is the result of the test. The six values in step 824 translate the single character results to field values for the test result.

In general terms, each step in a rules file indicates a character string to be found at a defined location in the line in the run file and a data format for the data values in the which uniquely identifies the data contained in the line. For lines which contain data that is to be stored into database records, the step in the rules file also indicates the field name of the data.

FIG. 8c is an example of a CMV type rules file as listed in the master rules file of FIG. 7. FIG. 8c shows examples of some of the other items of Table 1 not shown in the example of FIG. 8a.

c. Run File Parsing

Each line of the run file is treated as a separate entity, which means a data file cannot have a header record such as "POS CONTROLS" and then contain control values in the following lines. In other words, in the exemplary embodiment of the invention, each line of the run file contains a complete data item; a data item cannot be split across more than one line. It is contemplated that, in other embodiments of the invention, data items split across multiple lines may also be processed. It is also contemplated that run files may be processed which include multiple data items in a single line.

The evaluation of a line from a data file goes through four phases. If a line satisfies at least one rule in a phase, the line does not proceed to the next phase, but finishes all of the checks in the current phase.

Phase 1 checks each line to see if it contains a configured error. A configured error is an acceptable or known error that can be expected from the particular source. If an error is found, a configurable action (accept as NON-POSID, ignore, reject) is performed. If the action is reject, the batch data is rejected. In the exemplary embodiment of the present invention, a batch is defined as one or more trays which have a single set of control samples and to which a common test sequence is applied. As described above, the driver 510 may also receive a multiple batch input where each batch includes only a single tray. In this case, the driver 510 splits the input into separate and distinct run files, one for each batch.

If the action is ignore, no further processing is done on this line but the rest of the data is treated as valid. If the action is to accept the batch as NON-POSID, the type of the batch data is changed to NON-POSID which means the samples are dissociated from their sample ID's. This action requires that a successful data marriage, described below with reference to FIG. 9, be achieved before the batch data may be entered into the database 416.

Phase 2 checks each line in the run file to determine if it contains a header record. If a header record is found, this line is ignored and processing is allowed to continue.

Phase 3 checks for any non-sample information and, in so doing, builds a template to translate the file. The template information can be placed in a standalone file or can be in the form of flags placed in the original run file. The Phase 3 information includes the type of test that was run, the identity of the technician who ran it and information which governs how the results obtained from the batch are interpreted. Any given line can satisfy multiple rules in this section. Exemplary items checked in this phase are:

Batch Name, Procedure, Tray ID, Tech ID, Master Lot, Controls, Control Averages, Control Ranges, Control Differences, Cutoff, Cutoff Formula Phase 4 checks for the sample data. A batch is considered NON-POSID if no valid sample IDs can be read from the data file. If at least one sample ID can be read and verified, then the run is considered POSID. A sample ID is verified with the standard database sample verification routines. In the exemplary embodiment of the invention, the first digit of each sample identifier is a check-digit. The position of this digit may be changed by the administrator 540 or predemon 512 using a configurable parameter. In this instance, the sample verification routines determine if the sample ID is valid by recomputing this check-digit using the other digits in the sample ID. In general, the sample verification routines check the sample information for form and content based on the current system configuration. Exemplary items checked in this phase are:

Sample ID, Tray Position, Absorbance, Subbatch Information

If the post-demon 522 does not find a match for a given line in any of the phases, the line is ignored.

After the data file has been completely read, the final checks are performed. If the run is POSID and there were no errors, the batch data is entered into the database 416.

If the run is NON-POSID, two configuration parameters, which may be specified by the user, are checked and acted upon. The first configuration parameter indicates whether a data marriage operation is to be attempted. This operation is described below in the Data Marriage section with reference to FIG. 9. If the parameter indicates that a data marriage is allowed, the post-demon 522 attempts a data marriage operation. If data marriage is not allowed, the run will be considered NON-POSID.

The second configuration parameter determines whether NON-POSID batches may be entered into the database 416. If this parameter indicates that NON-POSID runs are allowed and the batch data is NON-POSID, then the run data is entered into the database 416. If NON-POSID runs are not allowed and the batch data is NON-POSID, the run data is rejected.

If the new run data has the same tray ID as unaccepted data that already exists on the system, the new run data overwrites the run data currently existing in the database 416.

d. Data Marriage

The data marriage section is used when a NON-POSID run is received. The run could have been initially NON-POSID or could have been converted to NON-POSID due to an error condition. In order to perform a data marriage, data from the data file is compared to data in the trays table (not shown) of the database 416. If a match is found, the samples are loaded and the status of the pipettor data is changed to archived. If the match is unsuccessful, the batch remains in its NON-POSID status. The data for this batch may be either accepted or rejected, as described above, as determined by a configuration parameter.

It should be noted that in the exemplary embodiment of the present invention, a slots table is maintained which correlates tray IDs to sample ids, thus, providing a one to many relation for trays and samples.

The minimum data required for a successful match is the tray ID, the procedure name or assay number, tray position, and the number of samples. If a match of these items is found, then the sample id's from the pipettor data for the batch can be attributed to the sample data in the run file. If a successful match is found, the samples are copied into the results table based on position number. After the data is copied, the batch is considered POSID.

Figure 9:
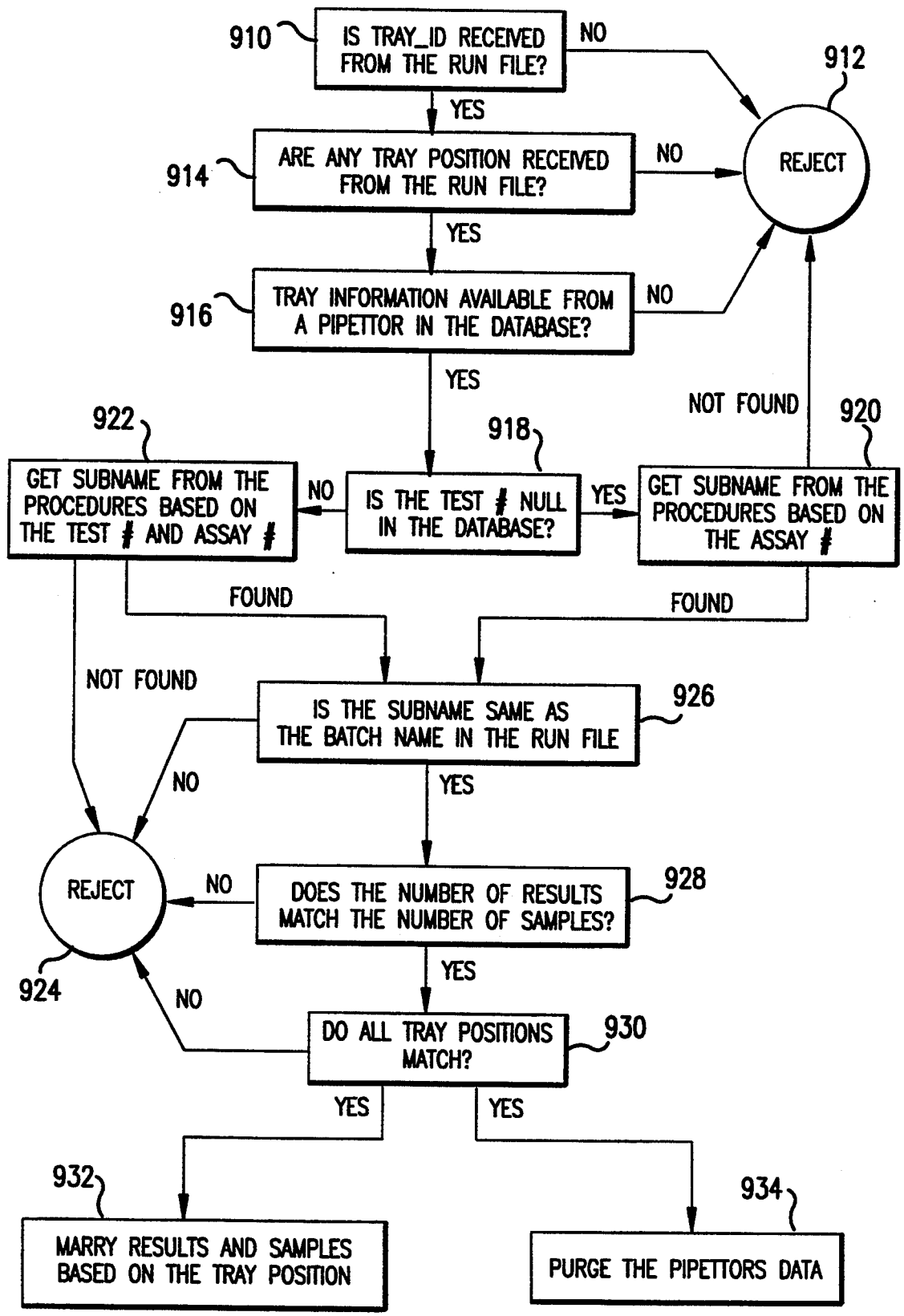
FIG. 9 is a flowchart diagram which illustrates the data marriage function which is performed in the data interfaces shown in FIGS. 5a and 5b.

The above-described process of a data marriage is summarized and presented as a flowchart in FIG. 9. In FIG. 9, at step 910, the Tray ID is received from the run file. If there is no Tray id, the data marriage fails and control is transferred to the reject step 912. If a tray ID is found at step 910, control is passed to step 914. This step determines if tray position information, indicating which of the tray positions contain samples, is available from the run file. If not, the marriage is rejected at step 912. If the position data is available then control is transferred to step 916. At step 916, the post-demon 522 determines if pipettor information corresponding to this tray ID is available in the database 416. If it is not, the marriage is rejected at step 912, otherwise control passes to step 918.

At step 918, the post-demon 522 checks the test number in the pipettor data which is stored in the database 416. If this test number is null, control is passed to step 920. This step attempts to get the sub name from the procedures table in database 416 using the assay number from the run file. If no subname information can be found, the marriage is rejected at step 912. If, however, subname information is found, then control passes to step 926.

At step 918, if the test number in the database 416 was not null, then, at step 922, the post-demon 522 attempts to get the subname data from the database 416 using the test number from the pipettor data and the assay number from the run data. If no test data can be found, the marriage is rejected at step 924. If, however, subname data is found, then control is passed to step 926.

At step 926, the subname data recovered from the database 416 is compared to the batch name in the run file. If these data do not match then the marriage is rejected at step 924, otherwise control passes to step 928. At step 928, if the number of results in the run file matches the number of samples in the pipettor data, control is passed to step 930, otherwise, the marriage is rejected at step 924.

At step 930, the post-demon 522 determines if the tray position data recovered at step 914 matches the pipettor data in the database 416. If any mismatch is found, the marriage is rejected at step 924. If the data are found to match, the sample ID data from the pipettor data in the database 416 is combined with the result data in the run file and the combined data is entered into the database 416. At the same time, the pipettor data in the database 416 is purged at step 934.

The present invention has been described in terms of exemplary embodiments. It is contemplated, however, that it may be practiced with modifications, some of which are outlined above, within the scope of the appended claims.

What is claimed:

1. A method of extracting individual items of biological test data from a plurality of data files, each of the data files being received from a corresponding source and having different locations for storing individual items of biological test data therein, comprising the steps of:
   receiving one of the data files from the corresponding source using a specified protocol;
   generating at least one run file from the received data file;
   examining the run file to identify specific locations of individual items of biological test data within the run file;
   assigning a rules file to the run file which indicates the identified locations; and
   parsing the run file with the assigned rules file to extract the individual items of biological test data within the run file.

2. The method of claim 1 further comprising the steps of:
   providing a master rules file comprising a plurality of different rules, each one of the rules specifying the location of at least one item of biological test data within the run file, and a rules file which indicates locations for individual items of biological test data within a run file; and
   assigning a match counter to each one of the plurality of rules within the master rules file.

3. The method of claim 2 wherein the examining step comprises the steps of:
   comparing each line of the run file with each one of the plurality of rules contained within the master rules file; and
   incrementing the assigned match counter for each one of the plurality of rules that matches a line within the run file.

4. The method of claim 3 wherein the assigning step comprises the steps of:
   determining which one of the plurality of rules has the greatest number of matches based upon the assigned match counters; and
   assigning the specified rules file from the determined one of the plurality of rules.

5. The method of claim 1 wherein the received data file comprises a tray Identification, an assay number, a tray position, and a plurality of samples.

6. The method of claim 5 further comprising the step of:
generating a slots table associated with the received data file, the slots table comprising tray and sample identifications for the received data file.

7. The method of claim 6 wherein the parsing step comprises the steps of:
parsing the run file with the assigned rules file to extract the individual items of biological test data within the run file; and
storing the extracted individual items of biological test data within an extracted file.

8. The method of claim 7 wherein the storing step comprises the step of:
merging the extracted individual items of biological test data with the slots table.

9. The method of claim 1 further comprising the steps of:
storing the extracted items of biological test data within an extracted file; and
storing the extracted file in a database.

10. The method of claim 1 wherein the generating step comprises the step of:
generating a plurality of run files from the received data file.

11. The method of claim 1 wherein said examining, assigning and parsing steps are performed simultaneously.

12. A system for extracting individual items of biological test data from a plurality of data files each of the data files being received from a corresponding source and having different locations for storing individual items of biological test data therein, comprising:
means for receiving one of the data files from the corresponding source using a specified protocol;
means for generating at least one run file from the received data file;
means for examining the run file to identify specific locations of individual items of biological test data within the run file;
means for assigning a rules file to the run file which indicates the identified locations; and
means for parsing the run file with the assigned rules file to extract the individual items of biological test data within the run file.

13. The system of claim 12 further comprising:
means for providing a master rules file comprising a plurality of different rules, each one of the rules specifying the location of at least one item of biological test data within the run file, and a rules file which indicates locations for individual items of biological test data within a run file; and
means for assigning a match counter to each one of the plurality of rules within the master rules file.

14. The system of claim 13 wherein the means for examining comprises:
means for comparing each line of the run file with each one of the plurality of rules contained within the master rules file; and
means for incrementing the assigned match counter for each one of the plurality of rules that matches a line within the run file.

15. The method of claim 14 wherein the means for assigning comprises:
means for determining which one of the plurality of rules has the greatest number of matches based upon the assigned match counters; and
means for assigning the specified rules file from the determined one of the plurality of rules.

16. The system of claim 12 wherein the received data file comprises a tray Identification, an assay number, a tray position, and a plurality of samples.

17. The system of claim 16 further comprising the step of:
means for generating a slots table associated with the received data file, the slots table comprising tray and sample identifications for the received data file.

18. The system of claim 17 wherein the means for parsing comprises:
means for parsing the run file with the assigned rules file to extract the individual items of biological test data within the run file; and
means for storing the extracted individual items of biological test data within an extracted file.

19. The system of claim 18 wherein the means for storing comprises:
means for merging the extracted individual items of biological test data with the slots table.

20. The system of claim 12 further comprising:
means for storing the extracted items of biological test data within an extracted file; and
means for storing the extracted file in a database.

21. The system of claim 12 wherein the means for generating comprises:
means for generating a plurality of run files from the received data file.

22. The system of claim 12 wherein said means for examining, assigning and parsing are performed simultaneously.

* * * * *